(12) United States Patent
Rai et al.

(10) Patent No.: US 9,611,196 B2
(45) Date of Patent: Apr. 4, 2017

(54) PROCESS FOR OBTAINING FOOD GRADE HEXANE

(71) Applicant: BHARAT PETROLEUM CORPORATION LTD, Mumbai (IN)

(72) Inventors: Pragya Rai, Surajpur (IN); Jose Nehamiah, Surajpur (IN); Chiranjeevi Thota, Surajpur (IN); Dattatraya Tammannashastri Gokak, Surajpur (IN); Poyyamani Swaminathan Viswanathan, Surajpur (IN); Shashikant Shukla, Maharashtra (IN); Buddhadeb Kundu, Maharashtra (IN); Satish Kumar Goel, Maharashtra (IN)

(73) Assignee: BHARAT PETROLEUM CORPORATION LTD, Mumbai (IN)

(*) Notice: Subject to any disclaimer, the term of this patent is extended or adjusted under 35 U.S.C. 154(b) by 277 days.

(21) Appl. No.: 14/233,324

(22) PCT Filed: Mar. 18, 2013

(86) PCT No.: PCT/IB2013/000406
§ 371 (c)(1),
(2) Date: Jan. 16, 2014

(87) PCT Pub. No.: WO2013/136169
PCT Pub. Date: Sep. 19, 2013

(65) Prior Publication Data
US 2015/0034474 A1 Feb. 5, 2015

(30) Foreign Application Priority Data
Mar. 16, 2012 (IN) ............................ 709/MUM/2012

(51) Int. Cl.
*C07C 7/10* (2006.01)
*B01D 11/04* (2006.01)
(Continued)

(52) U.S. Cl.
CPC ................ *C07C 7/10* (2013.01); *B01D 3/009* (2013.01); *B01D 3/143* (2013.01); *B01D 11/04* (2013.01);
(Continued)

(58) Field of Classification Search
CPC combination set(s) only.
See application file for complete search history.

(56) References Cited

U.S. PATENT DOCUMENTS 3,755,285 A * 8/1973 Piazza ................ B01D 11/0223
423/658.5
3,883,420 A * 5/1975 Stone .................... C10G 21/28
208/321

(Continued)

OTHER PUBLICATIONS

ISSE "Proceedings of International Symposium on Solvent Extraction", Sep. 26-27, 2002, p. 144 and 146.*

(Continued)

*Primary Examiner* — In Suk Bullock
*Assistant Examiner* — Ali Z Fadhel
(74) *Attorney, Agent, or Firm* — Stites & Harbison, PLLC; Mandy Wilson Decker; Rachel Rutledge

(57) ABSTRACT

The present invention relates to a process for obtaining food grade hexane, comprising: fractionating a hydrocarbon feed having a boiling point in the range of 50° C. to 140° C. to obtain a hydrocarbon fraction having boiling point in the range of 63° C. to 69° C. and having 3%-15% (wt/wt) of aromatic compounds content; extracting the hydrocarbon fraction by counter current solvent extraction using sulfolane as a solvent to obtain a first raffinate phase; extracting the first raffinate phase by co-current solvent extraction using sulfolane as a solvent to obtain a second raffinate phase; and washing the second raffinate phase with water to obtain a food grade hexane containing less than 100 ppm of aromatic compounds.

15 Claims, 3 Drawing Sheets

(51) Int. Cl.
*B01D 3/00* (2006.01)
*B01D 3/14* (2006.01)
*C07C 7/00* (2006.01)
*C07C 7/04* (2006.01)
*B01D 11/00* (2006.01)

(52) U.S. Cl.
CPC ............... *C07C 7/005* (2013.01); *C07C 7/04* (2013.01); *B01D 2011/002* (2013.01); *B01D 2011/005* (2013.01)

(56) References Cited

U.S. PATENT DOCUMENTS

| | | | | |
|---|---|---|---|---|
| 4,088,569 A | * | 5/1978 | Douglas | B01J 31/183 208/206 |
| 4,314,974 A | * | 2/1982 | Libby | B01D 11/0453 210/634 |
| 4,519,901 A | * | 5/1985 | Fiocco | C07C 7/10 208/321 |

OTHER PUBLICATIONS

Mahmoudi et al. "Extraction of benzene from a narrow cut of naphtha via liquid-liquid extraction using pure-sulfolane and 2-propanol-sulfolane-mixed solvents", Korean J. Chem. Eng., 27(1), 214-217, published 2010.*

* cited by examiner

PROCESS FOR OBTAINING FOOD GRADE HEXANE

TECHNICAL FIELD

The present invention relates to a process for obtaining food grade hexane from naphtha range hydrocarbon feed.

The food grade hexane obtained by the process has less than 100 ppm wt/wt of aromatic compounds.

BACKGROUND

The naphtha from petroleum industry contains varying amount of its constituent's viz. paraffins, naphthenes, aromatics and olefins in different proportion. Naphtha is used for different purposes depending on their boiling range and composition. They are mainly used in production of hydrogen, olefin, aromatics like Benzene, Toluene and Xylene, and as solvent in commercial and food industries. Narrow cut naphtha in the range of 63° C. to 69° C. with aromatics, mainly benzene, less than 650 ppm by weight known as food grade hexane is widely used in food industry. This low aromatic requirement of hexane is because of its application in the extraction of edible oil. Thus it is necessary to separate aromatics from the non aromatics phase to the extent possible.

The naphtha cut contains aromatics in the range of 3-15% and boiling point range from 50° C. to 140° C. depending on the petroleum crude and source of naphtha. Several processes such as catalytic hydrogenation, adsorptive dearomatisation, catalytic distillation and solvent extraction have been currently followed in industry for reduction of benzene in naphtha for the production of food grade hexane.

The catalytic hydrogenation involves the hydrogenation of benzene in liquid phase with the help of suspended solid. U.S. Pat. No. 3,505,421 describes a process of hydrogenating benzene in liquid phase by means of molecular hydrogen in the presence of suspended solid catalyst. U.S. Pat. No. 5,254,763 also describes a process for selective hydrogenation of benzene using water soluble organo-metallic hydrogenation catalyst. This hydrogenation process involves hydrogen at elevated temperature and pressure. The hydrogenation process also involves the removal of sulfur before the reaction, which makes this process more expensive.

The adsorptive dearomatisation was achieved using activated carbon, alumina, and zeolite materials. U.S. Pat. No. 3,963,934 claims the separation of aromatics from process streams by use of a molecular sieve. Other U.S. Pat. Nos. 2,728,800; 2,847,485; and 2,856,444 describes the use of silica gel for adsorbing aromatics from a process stream, followed by desorption by use of a liquid hydrocarbon. U.S. Pat. No. 5,294,334 describes the process for selectively removing benzene from gasoline boiling range process streams using aluminosilicate zeolite material.

The catalytic distillation for benzene removal is another method/technology. U.S. Pat. No. 7,501,549 claims the reduction in benzene from gasoline can be achieved by feeding a gasoline fraction with an alcohol and ether to a catalytic distillation column with one reaction zone containing an alkylation catalyst. Then the C6 hydrocarbons are separated from C7+ hydrocarbons.

The catalytic hydrogenation is another method for benzene removal where benzene reduction, olefin saturation and sulfur reduction occurs simultaneously. U.S. Pat. No. 6,153,805 discloses the catalytic hydrogenation of benzene to produce cyclo-hexane in the presence of metal catalyst. US Patent Application 2002/24395 discloses the production of food grade hexane by hydrogenation, using Ni supported alumina catalyst.

U.S. Pat. No. 4,428,829 reports the production of food grade hexane by separating aromatics and non-aromatics from heavy hydrocarbon stream by extraction process. The Indian patent applications 1224/DEL/1994 & 788/DEL/1994 discloses the separation of the aromatics and non-aromatics from naphtha and kerosene range fraction by extraction. The raffinate phase is water washed to remove the solvent carryover. The U.S. patent application 2001/82750 discloses the process for removal of aromatics from petroleum streams like naphtha, kerosene and gasoil through extraction by using solvents like NMP, Sulfolane and glycol. In all the above said process, solvent is recovered by distillation.

U.S. Pat. No. 3,551,327 discloses a process for recovery of aromatics from vapour to liquid phase i.e by extractive distillation, further it also focuses on raffinate water wash and recovery of sulfolane from water. US patent application 2001/82750 discloses a process for extraction of aromatics from petroleum fraction like heavy naphtha, kerosene and gas oil. U.S. Pat. Nos. 3,942,765, 4,314,974 discloses a process for the removal of metal ions from aqueous solution by using solvent in different type of static mixer and then whole process is confined to static mixer alone.

The processes for producing food grade hexane containing less than 100 ppm benzene is hydrogenation (U.S. patent application 2002/24395) and adsorption (U.S. Pat. No. 4,567,315). Refineries producing food grade hexane by solvent extraction process need to put up separate unit to employ these processes which is cost intensive.

Specifications for food grade hexane with respect to benzene content are becoming stringent day by day. Refineries producing food grade hexane by solvent extraction process need to switch to alternative processes like catalytic hydrogenation and adsorption which calls for additional capital investment. Thus there is a need for a cost effective process for obtaining a food grade hexane having less than 100 ppm of aromatic compound.

SUMMARY

The present invention relates to a process for obtaining food grade hexane, comprising: fractionating a hydrocarbon feed having a boiling point in the range of 50° C. to 140° C. to obtain a hydrocarbon fraction having boiling point in the range of 63° C. to 69° C. and having 3%-15% (wt/wt) of aromatic compounds content; extracting the hydrocarbon fraction by counter current solvent extraction using sulfolane as a solvent to obtain a first raffinate phase; extracting the first raffinate phase by co-current solvent extraction using sulfolane as a solvent to obtain a second raffinate phase; and washing the second raffinate phase with water to obtain a food grade hexane containing less than 100 ppm of aromatic compounds.

The present invention also relates to a process for obtaining food grade hexane, comprising: fractionating a hydrocarbon feed having a boiling point in the range of 50° C. to 140° C. to obtain a hydrocarbon fraction having boiling point in the range of 63° C. to 69° C. and having 3%-15% (wt/wt) of aromatic compounds content; extracting the hydrocarbon fraction by counter current solvent extraction using sulfolane as a solvent to obtain a first raffinate phase; extracting the first raffinate phase by co-current solvent extraction using sulfolane as a solvent to obtain a second raffinate phase; washing the second raffinate phase with water to obtain a food grade hexane containing less than 100 ppm of aromatic compounds; and recycling a part of the food grade hexane containing less than 100 ppm of aromatic compounds for the counter current solvent extraction.

These and other features, aspects, and advantages of the present subject matter will become better understood with reference to the following description and appended claims. This summary is provided to introduce a selection of concepts in a simplified form. This summary is not intended to identify key features or essential features of the claimed subject matter, nor is it intended to be used to limit the scope of the claimed subject matter.

BRIEF DESCRIPTION OF DRAWINGS

The above and other features, aspects, and advantages of the subject matter will become better understood with regard to the following description, appended claims, and accompanying drawings where:

DETAILED DESCRIPTION OF THE INVENTION

Figure 1:
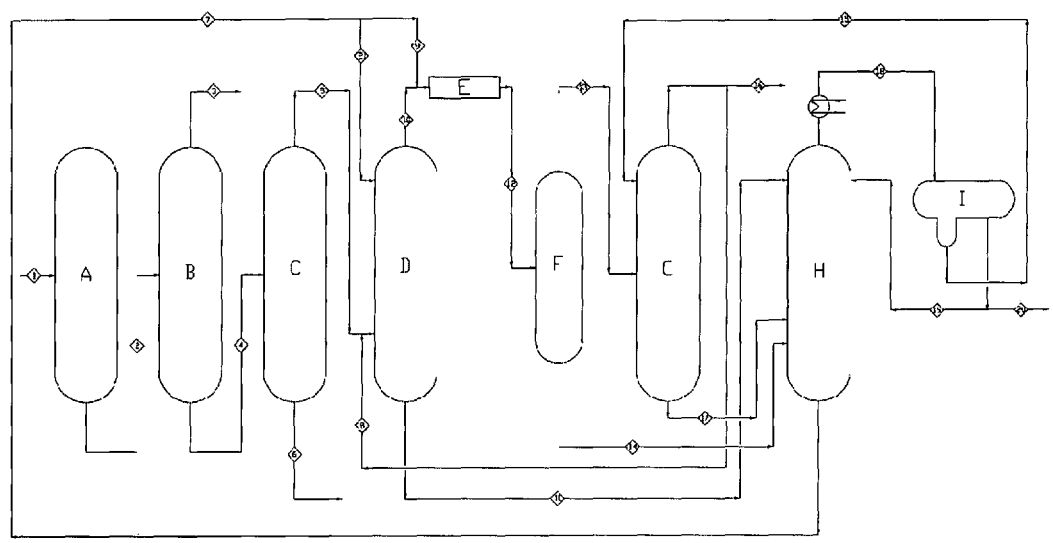
FIG. 1 is a schematic illustration of the process for obtaining food grade hexane containing less than 100 ppm aromatic compounds.

The present invention provides a process for obtaining food grade hexane, comprising: fractionating a hydrocarbon feed having a boiling point in the range of 50° C. to 140° C. to obtain a hydrocarbon fraction having boiling point in the range of 63° C. to 69° C. and having 3%-15% (wt/wt) of aromatic compounds content; extracting the hydrocarbon fraction by counter current solvent extraction using sulfolane as a solvent to obtain a first raffinate phase; extracting the first raffinate phase by co-current solvent extraction using sulfolane as a solvent to obtain a second raffinate phase; and washing the second raffinate phase with water to obtain a food grade hexane containing less than 100 ppm of aromatic compounds.

An embodiment of the present invention provides a process for obtaining food grade hexane, comprising: fractionating a the hydrocarbon feed having a boiling point in the range of 50° C. to 90° C. to obtain a hydrocarbon fraction having boiling point in the range of 63° C. to 69° C. and having 3%-15% (wt/wt) of aromatic compounds content; extracting the hydrocarbon fraction by counter current solvent extraction using sulfolane as a solvent to obtain a first raffinate phase; extracting the first raffinate phase by co-current solvent extraction using sulfolane as a solvent to obtain a second raffinate phase; and washing the second raffinate phase with water to obtain a food grade hexane containing less than 100 ppm of aromatic compounds.

Another embodiment of the present invention provides a process for obtaining food grade hexane, comprising: fractionating a naphtha range petroleum stock, having a boiling point in the range of 50° C. to 140° C. to obtain a hydrocarbon fraction having boiling point in the range of 63° C. to 69° C. and having 3%-15% (wt/wt) of aromatic compounds content; extracting the hydrocarbon fraction by counter current solvent extraction using sulfolane as a solvent to obtain a first raffinate phase; extracting the first raffinate phase by co-current solvent extraction using sulfolane as a solvent to obtain a second raffinate phase; and washing the second raffinate phase with water to obtain a food grade hexane containing less than 100 ppm of aromatic compounds.

Yet another embodiment of the present invention provides a process for obtaining food grade hexane, comprising: fractionating a hydrocarbon feed having a boiling point in the range of 50° C. to 140° C. to obtain a hydrocarbon fraction having boiling point in the range of 63° C. to 69° C. and having 3%-15% (wt/wt) of benzene; extracting the hydrocarbon fraction to remove benzene by counter current solvent extraction using sulfolane as a solvent to obtain a first raffinate phase; extracting the first raffinate phase by co-current solvent extraction using sulfolane as a solvent to obtain a second raffinate phase; and washing the second raffinate phase with water to obtain a food grade hexane containing less than 100 ppm of benzene.

Further an embodiment of the present invention provides a process for obtaining food grade hexane, comprising: fractionating a hydrocarbon feed having a boiling point in the range of 50° C. to 140° C. to obtain a hydrocarbon fraction having boiling point in the range of 63° C. to 69° C. and having 3%-15% (wt/wt) of toluene; extracting the hydrocarbon fraction to remove toluene by counter current solvent extraction using sulfolane as a solvent to obtain a first raffinate phase; extracting the first raffinate phase by co-current solvent extraction using sulfolane as a solvent to obtain a second raffinate phase; and washing the second raffinate phase with water to obtain a food grade hexane containing less than 100 ppm of toluene.

Another embodiment of the present invention provides a process for obtaining food grade hexane, comprising: fractionating a hydrocarbon feed having a boiling point in the range of 50° C. to 140° C. to obtain a hydrocarbon fraction having boiling point in the range of 63° C. to 69° C. and having 3%-15% (wt/wt) of mixture of benzene and toluene; extracting the hydrocarbon fraction to remove mixture of benzene and toluene by counter current solvent extraction using sulfolane as a solvent to obtain a first raffinate phase; extracting the first raffinate phase by co-current solvent extraction using sulfolane as a solvent to obtain a second raffinate phase; and washing the second raffinate phase with water to obtain a food grade hexane containing less than 100 ppm of mixture of benzene and toluene.

Still another embodiment of the present invention provides a process for obtaining food grade hexane, comprising: fractionating a hydrocarbon feed having a boiling point in the range of 50° C. to 140° C. to obtain a hydrocarbon fraction having boiling point in the range of 63° C. to 69° C. and having 3%-15% (wt/wt) of aromatic compounds content; extracting the hydrocarbon fraction by counter current solvent extraction using an extractor and sulfolane as a solvent to obtain a first raffinate phase; extracting the first raffinate phase by co-current solvent extraction using sulfolane as a solvent to obtain a second raffinate phase; and washing the second raffinate phase with water to obtain a food grade hexane containing less than 100 ppm of aromatic compounds.

Further an embodiment of the present invention provides a process for obtaining food grade hexane, comprising: fractionating a hydrocarbon feed having a boiling point in the range of 50° C. to 140° C. to obtain a hydrocarbon fraction having boiling point in the range of 63° C. to 69° C. and having 3%-15% (wt/wt) of aromatic compounds content; extracting the hydrocarbon fraction by counter current solvent extraction using a rotating disc column extractor and sulfolane as a solvent to obtain a first raffinate phase;

extracting the first raffinate phase by co-current solvent extraction using sulfolane as a solvent to obtain a second raffinate phase; and washing the second raffinate phase with water to obtain a food grade hexane containing less than 100 ppm of aromatic compounds.

Another embodiment of the present invention provides a process for obtaining food grade hexane, comprising: fractionating a hydrocarbon feed having a boiling point in the range of 50° C. to 140° C. to obtain a hydrocarbon fraction having boiling point in the range of 63° C. to 69° C. and having 3%-15% (wt/wt) of aromatic compounds content; extracting the hydrocarbon fraction by counter current solvent extraction using a packed column extractor and sulfolane as a solvent to obtain a first raffinate phase; extracting the first raffinate phase by co-current solvent extraction using sulfolane as a solvent to obtain a second raffinate phase; and washing the second raffinate phase with water to obtain a food grade hexane containing less than 100 ppm of aromatic compounds.

Still another embodiment of the present invention provides a process for obtaining food grade hexane, comprising: fractionating a hydrocarbon feed having a boiling point in the range of 50° C. to 140° C. to obtain a hydrocarbon fraction having boiling point in the range of 63° C. to 69° C. and having 3%-15% (wt/wt) of aromatic compounds content; extracting the hydrocarbon fraction by counter current solvent extraction using a sieve tray column extractor and sulfolane as a solvent to obtain a first raffinate phase; extracting the first raffinate phase by co-current solvent extraction using sulfolane as a solvent to obtain a second raffinate phase; and washing the second raffinate phase with water to obtain a food grade hexane containing less than 100 ppm of aromatic compounds.

Yet another embodiment of the present invention provides a process for obtaining food grade hexane, comprising: fractionating a hydrocarbon feed having a boiling point in the range of 50° C. to 140° C. to obtain a hydrocarbon fraction having boiling point in the range of 63° C. to 69° C. and having 3%-15% (wt/wt) of aromatic compounds content; extracting the hydrocarbon fraction by counter current solvent extraction using a pulsed column extractor and sulfolane as a solvent to obtain a first raffinate phase; extracting the first raffinate phase by co-current solvent extraction using sulfolane as a solvent to obtain a second raffinate phase; and washing the second raffinate phase with water to obtain a food grade hexane containing less than 100 ppm of aromatic compounds.

Another embodiment of the present invention provides a process for obtaining food grade hexane, comprising: fractionating a hydrocarbon feed having a boiling point in the range of 50° C. to 140° C. to obtain a hydrocarbon fraction having boiling point in the range of 63° C. to 69° C. and having 3%-15% (wt/wt) of aromatic compounds content; extracting the hydrocarbon fraction by counter current solvent extraction using a Karr reciprocating column extractor and sulfolane as a solvent to obtain a first raffinate phase; extracting the first raffinate phase by co-current solvent extraction using sulfolane as a solvent to obtain a second raffinate phase; and washing the second raffinate phase with water to obtain a food grade hexane containing less than 100 ppm of aromatic compounds.

Further an embodiment of the present invention provides a process for obtaining food grade hexane, comprising: fractionating a hydrocarbon feed having a boiling point in the range of 50° C. to 140° C. to obtain a hydrocarbon fraction having boiling point in the range of 63° C. to 69° C. and having 3%-15% (wt/wt) of aromatic compounds content; extracting the hydrocarbon fraction by counter current solvent extraction by counter currently mixing the sulfolane and the hydrocarbon fraction in a weight ratio in the range of 2 to 10 to obtain a first raffinate phase; extracting the first raffinate phase by co-current solvent extraction using sulfolane as a solvent to obtain a second raffinate phase; and washing the second raffinate phase with water to obtain a food grade hexane containing less than 100 ppm of aromatic compounds.

Yet another embodiment of the present invention provides a process for obtaining food grade hexane, comprising: fractionating a hydrocarbon feed having a boiling point in the range of 50° C. to 140° C. to obtain a hydrocarbon fraction having boiling point in the range of 63° C. to 69° C. and having 3%-15% (wt/wt) of aromatic compounds content; extracting the hydrocarbon fraction by counter current solvent extraction using sulfolane as a solvent to obtain a first raffinate phase; extracting the first raffinate phase by co-current solvent extraction using a static mixer, and sulfolane as a solvent to obtain a second raffinate phase; and washing the second raffinate phase with water to obtain a food grade hexane containing less than 100 ppm of aromatic compounds.

Still another embodiment of the present invention provides a process for obtaining food grade hexane, comprising: fractionating a hydrocarbon feed having a boiling point in the range of 50° C. to 140° C. to obtain a hydrocarbon fraction having boiling point in the range of 63° C. to 69° C. and having 3%-15% (wt/wt) of aromatic compounds content; extracting the hydrocarbon fraction by counter current solvent extraction using sulfolane as a solvent to obtain a first raffinate phase; extracting the first raffinate phase by co-current solvent extraction using a corrugated plate static mixer and sulfolane as a solvent to obtain a second raffinate phase; and washing the second raffinate phase with water to obtain a food grade hexane containing less than 100 ppm of aromatic compounds.

Another embodiment of the present invention provides a process for obtaining food grade hexane, comprising: fractionating a hydrocarbon feed having a boiling point in the range of 50° C. to 140° C. to obtain a hydrocarbon fraction having boiling point in the range of 63° C. to 69° C. and having 3%-15% (wt/wt) of aromatic compounds content; extracting the hydrocarbon fraction by counter current solvent extraction using sulfolane as a solvent to obtain a first raffinate phase; extracting the first raffinate phase by co-current solvent extraction using a multilayer static mixer and sulfolane as a solvent to obtain a second raffinate phase; and washing the second raffinate phase with water to obtain a food grade hexane containing less than 100 ppm of aromatic compounds.

Still, another embodiment of the present invention provides a process for obtaining food grade hexane, comprising: fractionating a hydrocarbon feed having a boiling point in the range of 50° C. to 140° C. to obtain a hydrocarbon fraction having boiling point in the range of 63° C. to 69° C. and having 3%-15% (wt/wt) of aromatic compounds content; extracting the hydrocarbon fraction by counter current solvent extraction using sulfolane as a solvent to obtain a first raffinate phase; extracting the first raffinate phase by co-current solvent extraction using a open design with helical static mixer and sulfolane as a solvent to obtain a second raffinate phase; and washing the second raffinate phase with water to obtain a food grade hexane containing less than 100 ppm of aromatic compounds.

Yet another embodiment of the present invention provides a process for obtaining food grade hexane, comprising:

fractionating a hydrocarbon feed having a boiling point in the range of 50° C. to 140° C. to obtain a hydrocarbon fraction having boiling point in the range of 63° C. to 69° C. and having 3%-15% (wt/wt) of aromatic compounds content; extracting the hydrocarbon fraction by counter current solvent extraction using sulfolane as a solvent to obtain a first raffinate phase; extracting the first raffinate phase by co-current solvent extraction using a open design with blades static mixer and sulfolane as a solvent to obtain a second raffinate phase; and washing the second raffinate phase with water to obtain a food grade hexane containing less than 100 ppm of aromatic compounds.

Further an embodiment of the present invention provides a process for obtaining food grade hexane, comprising: fractionating a hydrocarbon feed having a boiling point in the range of 50° C. to 140° C. to obtain a hydrocarbon fraction having boiling point in the range of 63° C. to 69° C. and having 3%-15% (wt/wt) of aromatic compounds content; extracting the hydrocarbon fraction by counter current solvent extraction using sulfolane as a solvent to obtain a first raffinate phase; extracting the first raffinate phase by co-current solvent extraction which is carried out by co-currently mixing the sulfolane and the first raffinate phase in a weight ratio in the range of 2 to 10 to obtain a second raffinate phase; and washing the second raffinate phase with water to obtain a food grade hexane containing less than 100 ppm of aromatic compounds.

Another embodiment of the present invention provides a process for obtaining food grade hexane, comprising: fractionating a hydrocarbon feed having a boiling point in the range of 50° C. to 140° C. to obtain a hydrocarbon fraction having boiling point in the range of 63° C. to 69° C. and having 3%-15% (wt/wt) of aromatic compounds content; extracting the hydrocarbon fraction by counter current solvent extraction which is carried out at a temperature in the range of 50° C. to 110° C. using sulfolane as a solvent to obtain a first raffinate phase; extracting the first raffinate phase by co-current solvent extraction using sulfolane as a solvent to obtain a second raffinate phase; and washing the second raffinate phase with water to obtain a food grade hexane containing less than 100 ppm of aromatic compounds.

Yet another embodiment of the present invention provides a process for obtaining food grade hexane, comprising: fractionating a hydrocarbon feed having a boiling point in the range of 50° C. to 140° C. to obtain a hydrocarbon fraction having boiling point in the range of 63° C. to 69° C. and having 3%-15% (wt/wt) of aromatic compounds content; extracting the hydrocarbon fraction by counter current solvent extraction using sulfolane as a solvent to obtain a first raffinate phase; extracting the first raffinate phase by co-current solvent extraction which is carried out at a temperature in the range of 50° C. to 110° C. using sulfolane as a solvent to obtain a second raffinate phase; and washing the second raffinate phase with water to obtain a food grade hexane containing less than 100 ppm of aromatic compounds.

The present invention further relates to a process for obtaining food grade hexane, comprising: fractionating a hydrocarbon feed having a boiling point in the range of 50° C. to 140° C. to obtain a hydrocarbon fraction having boiling point in the range of 63° C. to 69° C. and having 3%-15% (wt/wt) of aromatic compounds content; extracting the hydrocarbon fraction by counter current solvent extraction using sulfolane as a solvent to obtain a first raffinate phase; extracting the first raffinate phase by co-current solvent extraction using sulfolane as a solvent to obtain a second raffinate phase; washing the second raffinate phase with water to obtain a food grade hexane containing less than 100 ppm of aromatic compounds; and recycling a part of the food grade hexane containing less than 100 ppm of aromatic compounds for the counter current solvent extraction.

An embodiment of the present invention provides a process for obtaining food grade hexane, comprising: fractionating the hydrocarbon feed having a boiling point in the range of 50° C. to 90° C. to obtain a hydrocarbon fraction having boiling point in the range of 63° C. to 69° C. and having 3%-15% (wt/wt) of aromatic compounds content; extracting the hydrocarbon fraction by counter current solvent extraction using sulfolane as a solvent to obtain a first raffinate phase; extracting the first raffinate phase by co-current solvent extraction using sulfolane as a solvent to obtain a second raffinate phase; washing the second raffinate phase with water to obtain a food grade hexane containing less than 100 ppm of aromatic compounds; and recycling a part of the food grade hexane containing less than 100 ppm of aromatic compounds for the counter current solvent extraction.

Another embodiment of the present invention provides a process for obtaining food grade hexane, comprising: fractionating a naphtha range petroleum stock to obtain a hydrocarbon fraction having boiling point in the range of 63° C. to 69° C. and having 3%-15% (wt/wt) of aromatic compounds content; extracting the hydrocarbon fraction by counter current solvent extraction using sulfolane as a solvent to obtain a first raffinate phase; extracting the first raffinate phase by co-current solvent extraction using sulfolane as a solvent to obtain a second raffinate phase; washing the second raffinate phase with water to obtain a food grade hexane containing less than 100 ppm of aromatic compounds; and recycling a part of the food grade hexane containing less than 100 ppm of aromatic compounds for the counter current solvent extraction.

Yet another embodiment of the present invention provides a process for obtaining food grade hexane, comprising: fractionating a hydrocarbon feed having a boiling point in the range of 50° C. to 140° C. to obtain a hydrocarbon fraction having boiling point in the range of 63° C. to 69° C. and having 3%-15% (wt/wt) of benzene; extracting the hydrocarbon fraction to remove benzene by counter current solvent extraction using sulfolane as a solvent to obtain a first raffinate phase; extracting the first raffinate phase by co-current solvent extraction using sulfolane as a solvent to obtain a second raffinate phase; washing the second raffinate phase with water to obtain a food grade hexane containing less than 100 ppm of benzene; and recycling a part of the food grade hexane containing less than 100 ppm of benzene for the counter current solvent extraction.

Another embodiment of the present invention provides a process for obtaining food grade hexane, comprising: fractionating a hydrocarbon feed having a boiling point in the range of 50° C. to 140° C. to obtain a hydrocarbon fraction having boiling point in the range of 63° C. to 69° C. and having 3%-15% (wt/wt) of toluene; extracting the hydrocarbon fraction to remove toluene by counter current solvent extraction using sulfolane as a solvent to obtain a first raffinate phase; extracting the first raffinate phase by co-current solvent extraction using sulfolane as a solvent to obtain a second raffinate phase; washing the second raffinate phase with water to obtain a food grade hexane containing less than 100 ppm of toluene; and recycling a part of the food grade hexane containing less than 100 ppm of toluene for the counter current solvent extraction.

Further, an embodiment of the present invention provides a process for obtaining food grade hexane, comprising: fractionating a hydrocarbon feed having a boiling point in the range of 50° C. to 140° C. to obtain a hydrocarbon fraction having boiling point in the range of 63° C. to 69° C. and having 3%-15% (wt/wt) of mixture of benzene and toluene; extracting the hydrocarbon fraction to remove the mixture of benzene and toluene by counter current solvent extraction using sulfolane as a solvent to obtain a first raffinate phase; extracting the first raffinate phase by co-current solvent extraction using sulfolane as a solvent to obtain a second raffinate phase; washing the second raffinate phase with water to obtain a food grade hexane containing less than 100 ppm of mixture of benzene and toluene; and recycling a part of the food grade hexane containing less than 100 ppm of mixture of benzene and toluene for the counter current solvent extraction.

Still another embodiment of the present invention provides a process for obtaining food grade hexane, comprising: fractionating a hydrocarbon feed having a boiling point in the range of 50° C. to 140° C. to obtain a hydrocarbon fraction having boiling point in the range of 63° C. to 69° C. and having 3%-15% (wt/wt) of aromatic compounds content; extracting the hydrocarbon fraction by counter current solvent extraction using an extractor, and sulfolane as a solvent to obtain a first raffinate phase; extracting the first raffinate phase by co-current solvent extraction using sulfolane as a solvent to obtain a second raffinate phase; washing the second raffinate phase with water to obtain a food grade hexane containing less than 100 ppm of aromatic compounds; and recycling a part of the food grade hexane containing less than 100 ppm of aromatic compounds for the counter current solvent extraction.

Further an embodiment of the present invention provides a process for obtaining food grade hexane, comprising: fractionating a hydrocarbon feed having a boiling point in the range of 50° C. to 140° C. to obtain a hydrocarbon fraction having boiling point in the range of 63° C. to 69° C. and having 3%-15% (wt/wt) of aromatic compounds content; extracting the hydrocarbon fraction by counter current solvent extraction using rotating disc column and sulfolane as a solvent to obtain a first raffinate phase; extracting the first raffinate phase by co-current solvent extraction using sulfolane as a solvent to obtain a second raffinate phase; washing the second raffinate phase with water to obtain a food grade hexane containing less than 100 ppm of aromatic compounds; and recycling a part of the food grade hexane containing less than 100 ppm of aromatic compounds for the counter current solvent extraction.

Yet another embodiment of the present invention provides a process for obtaining food grade hexane, comprising: fractionating a hydrocarbon feed having a boiling point in the range of 50° C. to 140° C. to obtain a hydrocarbon fraction having boiling point in the range of 63° C. to 69° C. and having 3%-15% (wt/wt) of aromatic compounds content; extracting the hydrocarbon fraction by counter current solvent extraction using packed column and sulfolane as a solvent to obtain a first raffinate phase; extracting the first raffinate phase by co-current solvent extraction using sulfolane as a solvent to obtain a second raffinate phase; washing the second raffinate phase with water to obtain a food grade hexane containing less than 100 ppm of aromatic compounds; and recycling a part of the food grade hexane containing less than 100 ppm of aromatic compounds for the counter current solvent extraction.

Further an embodiment of the present invention provides a process for obtaining food grade hexane, comprising: fractionating a hydrocarbon feed having a boiling point in the range of 50° C. to 140° C. to obtain a hydrocarbon fraction having boiling point in the range of 63° C. to 69° C. and having 3%-15% (wt/wt) of aromatic compounds content; extracting the hydrocarbon fraction by counter current solvent extraction using Sieve tray column and sulfolane as a solvent to obtain a first raffinate phase; extracting the first raffinate phase by co-current solvent extraction using sulfolane as a solvent to obtain a second raffinate phase; washing the second raffinate phase with water to obtain a food grade hexane containing less than 100 ppm of aromatic compounds; and recycling a part of the food grade hexane containing less than 100 ppm of aromatic compounds for the counter current solvent extraction.

Still another embodiment of the present invention provides a process for obtaining food grade hexane, comprising: fractionating a hydrocarbon feed having a boiling point in the range of 50° C. to 140° C. to obtain a hydrocarbon fraction having boiling point in the range of 63° C. to 69° C. and having 3%-15% (wt/wt) of aromatic compounds content; extracting the hydrocarbon fraction by counter current solvent extraction using pulsed column and sulfolane as a solvent to obtain a first raffinate phase; extracting the first raffinate phase by co-current solvent extraction using sulfolane as a solvent to obtain a second raffinate phase; washing the second raffinate phase with water to obtain a food grade hexane containing less than 100 ppm of aromatic compounds; and recycling a part of the food grade hexane containing less than 100 ppm of aromatic compounds for the counter current solvent extraction.

Yet another embodiment of the present invention provides a process for obtaining food grade hexane, comprising: fractionating a hydrocarbon feed having a boiling point in the range of 50° C. to 140° C. to obtain a hydrocarbon fraction having boiling point in the range of 63° C. to 69° C. and having 3%-15% (wt/wt) of aromatic compounds content; extracting the hydrocarbon fraction by counter current solvent extraction using Karr reciprocating column and sulfolane as a solvent to obtain a first raffinate phase; extracting the first raffinate phase by co-current solvent extraction using sulfolane as a solvent to obtain a second raffinate phase; washing the second raffinate phase with water to obtain a food grade hexane containing less than 100 ppm of aromatic compounds; and recycling a part of the food grade hexane containing less than 100 ppm of aromatic compounds for the counter current solvent extraction.

Another embodiment of the present invention provides a process for obtaining food grade hexane, comprising: fractionating a hydrocarbon feed having a boiling point in the range of 50° C. to 140° C. to obtain a hydrocarbon fraction having boiling point in the range of 63° C. to 69° C. and having 3%-15% (wt/wt) of aromatic compounds content; extracting the hydrocarbon fraction by counter current solvent extraction which is carried out by counter currently mixing the sulfolane and the hydrocarbon fraction in a weight ratio in the range of 2 to 10 to obtain a first raffinate phase; extracting the first raffinate phase by co-current solvent extraction using sulfolane as a solvent to obtain a second raffinate phase; washing the second raffinate phase with water to obtain a food grade hexane containing less than 100 ppm of aromatic compounds; and recycling a part of the food grade hexane containing less than 100 ppm of aromatic compounds for the counter current solvent extraction.

Yet another embodiment of the present invention provides a process for obtaining food grade hexane, comprising: fractionating a hydrocarbon feed having a boiling point in the range of 50° C. to 140° C. to obtain a hydrocarbon fraction having boiling point in the range of 63° C. to 69° C. and having 3%-15% (wt/wt) of aromatic compounds content; extracting the hydrocarbon fraction by counter current solvent extraction using sulfolane as a solvent to obtain a first raffinate phase; extracting the first raffinate phase by co-current solvent extraction using a static mixer, and sulfolane as a solvent to obtain a second raffinate phase; washing the second raffinate phase with water to obtain a food grade hexane containing less than 100 ppm of aromatic compounds; and recycling a part of the food grade hexane containing less than 100 ppm of aromatic compounds for the counter current solvent extraction.

Still another embodiment of the present invention provides a process for obtaining food grade hexane, comprising: fractionating a hydrocarbon feed having a boiling point in the range of 50° C. to 140° C. to obtain a hydrocarbon fraction having boiling point in the range of 63° C. to 69° C. and having 3%-15% (wt/wt) of aromatic compounds content; extracting the hydrocarbon fraction by counter current solvent extraction using sulfolane as a solvent to obtain a first raffinate phase; extracting the first raffinate phase by co-current solvent extraction by using a corrugated plate static mixer and sulfolane as a solvent to obtain a second raffinate phase; washing the second raffinate phase with water to obtain a food grade hexane containing less than 100 ppm of aromatic compounds; and recycling a part of the food grade hexane containing less than 100 ppm of aromatic compounds for the counter current solvent extraction.

Still another embodiment of the present invention provides a process for obtaining food grade hexane, comprising: fractionating a hydrocarbon feed having a boiling point in the range of 50° C. to 140° C. to obtain a hydrocarbon fraction having boiling point in the range of 63° C. to 69° C. and having 3%-15% (wt/wt) of aromatic compounds content; extracting the hydrocarbon fraction by counter current solvent extraction using sulfolane as a solvent to obtain a first raffinate phase; extracting the first raffinate phase by co-current solvent extraction by using a multilayer static mixer and sulfolane as a solvent to obtain a second raffinate phase; washing the second raffinate phase with water to obtain a food grade hexane containing less than 100 ppm of aromatic compounds; and recycling a part of the food grade hexane containing less than 100 ppm of aromatic compounds for the counter current solvent extraction.

Still another embodiment of the present invention provides a process for obtaining food grade hexane, comprising: fractionating a hydrocarbon feed having a boiling point in the range of 50° C. to 140° C. to obtain a hydrocarbon fraction having boiling point in the range of 63° C. to 69° C. and having 3%-15% (wt/wt) of aromatic compounds content; extracting the hydrocarbon fraction by counter current solvent extraction using sulfolane as a solvent to obtain a first raffinate phase; extracting the first raffinate phase by co-current solvent extraction by using a open design with helical static mixer and sulfolane as a solvent to obtain a second raffinate phase; washing the second raffinate phase with water to obtain a food grade hexane containing less than 100 ppm of aromatic compounds; and recycling a part of the food grade hexane containing less than 100 ppm of aromatic compounds for the counter current solvent extraction.

Still another embodiment of the present invention provides a process for obtaining food grade hexane, comprising: fractionating a hydrocarbon feed having a boiling point in the range of 50° C. to 140° C. to obtain a hydrocarbon fraction having boiling point in the range of 63° C. to 69° C. and having 3%-15% (wt/wt) of aromatic compounds content; extracting the hydrocarbon fraction by counter current solvent extraction using sulfolane as a solvent to obtain a first raffinate phase; extracting the first raffinate phase by co-current solvent extraction by using a open design with blades static mixer and sulfolane as a solvent to obtain a second raffinate phase; washing the second raffinate phase with water to obtain a food grade hexane containing less than 100 ppm of aromatic compounds; and recycling a part of the food grade hexane containing less than 100 ppm of aromatic compounds for the counter current solvent extraction.

Further an embodiment of the present invention provides a process for obtaining food grade hexane, comprising: fractionating a hydrocarbon feed having a boiling point in the range of 50° C. to 140° C. to obtain a hydrocarbon fraction having boiling point in the range of 63° C. to 69° C. and having 3%-15% (wt/wt) of aromatic compounds content; extracting the hydrocarbon fraction by counter current solvent extraction using sulfolane as a solvent to obtain a first raffinate phase; extracting the first raffinate phase by co-current solvent extraction which is carried out by co-currently mixing the sulfolane and the first raffinate phase in a weight ratio in the range of 2 to 10 to obtain a second raffinate phase; washing the second raffinate phase with water to obtain a food grade hexane containing less than 100 ppm of aromatic compounds; and recycling a part of the food grade hexane containing less than 100 ppm of aromatic compounds for the counter current solvent extraction.

Another embodiment of the present invention provides a process for obtaining food grade hexane, comprising: fractionating a hydrocarbon feed having a boiling point in the range of 50° C. to 140° C. to obtain a hydrocarbon fraction having boiling point in the range of 63° C. to 69° C. and having 3%-15% (wt/wt) of aromatic compounds content; extracting the hydrocarbon fraction by counter current solvent extraction which is carried out at a temperature in the range of 50° C. to 110° C. using sulfolane as a solvent to obtain a first raffinate phase; extracting the first raffinate phase by co-current solvent extraction using sulfolane as a solvent to obtain a second raffinate phase; washing the second raffinate phase with water to obtain a food grade hexane containing less than 100 ppm of aromatic compounds; and recycling a part of the food grade hexane containing less than 100 ppm of aromatic compounds for the counter current solvent extraction.

Yet another embodiment of the present invention provides a process for obtaining food grade hexane, comprising: fractionating a hydrocarbon feed having a boiling point in the range of 50° C. to 140° C. to obtain a hydrocarbon fraction having boiling point in the range of 63° C. to 69° C. and having 3%-15% (wt/wt) of aromatic compounds content; extracting the hydrocarbon fraction by counter current solvent extraction using sulfolane as a solvent to obtain a first raffinate phase; extracting the first raffinate phase by co-current solvent extraction is carried out at a temperature in the range of 50° C. to 110° C. using sulfolane as a solvent to obtain a second raffinate phase; washing the second raffinate phase with water to obtain a food grade hexane containing less than 100 ppm of aromatic compounds; and recycling a part of the food grade hexane containing less than 100 ppm of aromatic compounds for the counter current solvent extraction.

The present invention further provides a process for obtaining food grade hexane, comprising: treating a hydrocarbon feed having a boiling point in the range of 50° C. to 140° C. to obtain a mercaptan free hydrocarbon feed by converting mercaptan content of the hydrocarbon feed into disulfide; fractionating the mercaptan free hydrocarbon feed having a boiling point in the range of 50° C. to 140° C. to obtain a hydrocarbon fraction having boiling point in the range of 63° C. to 69° C. and having 3%-15% (wt/wt) of aromatic compounds content; extracting the hydrocarbon fraction by counter current solvent extraction using sulfolane as a solvent to obtain a first raffinate phase; extracting the first raffinate phase by co-current solvent extraction using sulfolane as a solvent to obtain a second raffinate phase; washing the second raffinate phase with water to obtain a food grade hexane containing less than 100 ppm of aromatic compounds; and recycling a part of the food grade hexane containing less than 100 ppm of aromatic compounds for the counter current solvent extraction.

An embodiment of the present invention provides a process for obtaining food grade hexane, comprising: treating a hydrocarbon feed having a boiling point in the range of 50° C. to 90° C. to obtain a mercaptan free hydrocarbon feed by converting mercaptan content of the hydrocarbon feed into disulfide; fractionating the mercaptan free hydrocarbon feed having a boiling point in the range of 50° C. to 90° C. to obtain a hydrocarbon fraction having boiling point in the range of 63° C. to 69° C. and having 3%-15% (wt/wt) of aromatic compounds content; extracting the hydrocarbon fraction by counter current solvent extraction using sulfolane as a solvent to obtain a first raffinate phase; extracting the first raffinate phase by co-current solvent extraction using sulfolane as a solvent to obtain a second raffinate phase; washing the second raffinate phase with water to obtain a food grade hexane containing less than 100 ppm of aromatic compounds; and recycling a part of the food grade hexane containing less than 100 ppm of aromatic compounds for the counter current solvent extraction.

Another embodiment of the present invention provides a process for obtaining food grade hexane, comprising: treating a naphtha range petroleum stock to obtain a mercaptan free naphtha range petroleum stock by converting mercaptan content of the naphtha range petroleum stock into disulfide; fractionating the mercaptan free naphtha range petroleum stock to obtain a hydrocarbon fraction having boiling point in the range of 63° C. to 69° C. and having 3%-15% (wt/wt) of aromatic compounds content; extracting the hydrocarbon fraction by counter current solvent extraction using sulfolane as a solvent to obtain a first raffinate phase; extracting the first raffinate phase by co-current solvent extraction using sulfolane as a solvent to obtain a second raffinate phase; washing the second raffinate phase with water to obtain a food grade hexane containing less than 100 ppm of aromatic compounds; and recycling a part of the food grade hexane containing less than 100 ppm of aromatic compounds for the counter current solvent extraction.

Yet another embodiment of the present invention provides a process for obtaining food grade hexane, comprising: treating a hydrocarbon feed having a boiling point in the range of 50° C. to 140° C. to obtain a mercaptan free hydrocarbon feed by converting mercaptan content of the hydrocarbon feed into disulfide to; fractionating the mercaptan free hydrocarbon feed having a boiling point in the range of 50° C. to 140° C. to obtain a hydrocarbon fraction having boiling point in the range of 63° C. to 69° C. and having 3%-15% (wt/wt) of benzene; extracting the hydrocarbon fraction to remove benzene by counter current solvent extraction using sulfolane as a solvent to obtain a first raffinate phase; extracting the first raffinate phase by co-current solvent extraction using sulfolane as a solvent to obtain a second raffinate phase; washing the second raffinate phase with water to obtain a food grade hexane containing less than 100 ppm of benzene; and recycling a part of the food grade hexane containing less than 100 ppm of benzene for the counter current solvent extraction.

Another embodiment of the present invention provides a process for obtaining food grade hexane, comprising: treating a hydrocarbon feed having a boiling point in the range of 50° C. to 140° C. to to obtain a mercaptan free hydrocarbon feed by converting mercaptan content of the hydrocarbon feed into disulfide; fractionating the mercaptan free hydrocarbon feed having a boiling point in the range of 50° C. to 140° C. to obtain a hydrocarbon fraction having boiling point in the range of 63° C. to 69° C. and having 3%-15% (wt/wt) of toluene; extracting the hydrocarbon fraction to remove toluene by counter current solvent extraction using sulfolane as a solvent to obtain a first raffinate phase; extracting the first raffinate phase by co-current solvent extraction using sulfolane as a solvent to obtain a second raffinate phase; washing the second raffinate phase with water to obtain a food grade hexane containing less than 100 ppm of toluene; and recycling a part of the food grade hexane containing less than 100 ppm of toluene for the counter current solvent extraction.

Still another embodiment of the present invention provides a process for obtaining food grade hexane, comprising: treating a hydrocarbon feed having a boiling point in the range of 50° C. to 140° C. to obtain a mercaptan free hydrocarbon feed by converting mercaptan content of the hydrocarbon feed into disulfide; fractionating the mercaptan free hydrocarbon feed having a boiling point in the range of 50° C. to 140° C. to obtain a hydrocarbon fraction having boiling point in the range of 63° C. to 69° C. and having 3%-15% (wt/wt) of mixture of benzene and toluene; extracting the hydrocarbon fraction to remove the mixture of benzene and toluene by counter current solvent extraction using sulfolane as a solvent to obtain a first raffinate phase; extracting the first raffinate phase by co-current solvent extraction using sulfolane as a solvent to obtain a second raffinate phase; washing the second raffinate phase with water to obtain a food grade hexane containing less than 100 ppm of the mixture of benzene and toluene; and recycling a part of the food grade hexane containing less than 100 ppm of the mixture of benzene and toluene for the counter current solvent extraction.

Still another embodiment of the present invention provides a process for obtaining food grade hexane, comprising: treating a hydrocarbon feed having a boiling point in the range of 50° C. to 140° C. to obtain a mercaptan free hydrocarbon feed by converting mercaptan content of the hydrocarbon feed into disulfide; fractionating the mercaptan free hydrocarbon feed having a boiling point in the range of 50° C. to 140° C. to obtain a hydrocarbon fraction having boiling point in the range of 63° C. to 69° C. and having 3%-15% (wt/wt) of aromatic compounds content; extracting the hydrocarbon fraction by counter current solvent extraction using an extractor, and sulfolane as a solvent to obtain a first raffinate phase; extracting the first raffinate phase to obtain a second raffinate phase by co-current solvent extraction using sulfolane as a solvent; washing the second raffinate phase with water to obtain a food grade hexane containing less than 100 ppm of aromatic compounds; and recycling a part of the food grade hexane containing less than 100 ppm of aromatic compounds for the counter current solvent extraction.

Another embodiment of the present invention provides a process for obtaining food grade hexane, comprising: treating a hydrocarbon feed having a boiling point in the range of 50° C. to 140° C. to obtain a mercaptan free hydrocarbon feed by converting mercaptan content of the hydrocarbon feed into disulfide; fractionating the mercaptan free hydrocarbon feed having a boiling point in the range of 50° C. to 140° C. to obtain a hydrocarbon fraction having boiling point in the range of 63° C. to 69° C. and having 3%-15% (wt/wt) of aromatic compounds content; extracting the hydrocarbon fraction by counter current solvent extraction which is carried out by counter currently mixing the sulfolane and the hydrocarbon fraction in a weight ratio in the range of 2 to 10 to obtain a first raffinate phase; extracting the first raffinate phase by co-current solvent extraction using sulfolane as a solvent to obtain a second raffinate phase; washing the second raffinate phase with water to obtain a food grade hexane containing less than 100 ppm of aromatic compounds; and recycling a part of the food grade hexane containing less than 100 ppm of aromatic compounds for the counter current solvent extraction.

The extractor used in the process of the present invention for counter current solvent extraction is usually selected from, but not limited to the group consisting of rotating disc column, packed column, Sieve tray column, pulsed column, and Karr reciprocating column.

Yet another embodiment of the present invention provides a process for obtaining food grade hexane, comprising: treating a hydrocarbon feed having a boiling point in the range of 50° C. to 140° C. to obtain a mercaptan free hydrocarbon feed by converting mercaptan content of the hydrocarbon feed into disulfide; fractionating the mercaptan free hydrocarbon feed having a boiling point in the range of 50° C. to 140° C. to obtain a hydrocarbon fraction having boiling point in the range of 63° C. to 69° C. and having 3%-15% (wt/wt) of aromatic compounds content; extracting the hydrocarbon fraction by counter current solvent extraction using sulfolane as a solvent to obtain a first raffinate phase; extracting the first raffinate phase by co-current solvent extraction using a static mixer, using sulfolane as a solvent to obtain a second raffinate phase; washing the second raffinate phase with water to obtain a food grade hexane containing less than 100 ppm of aromatic compounds; and recycling a part of the food grade hexane containing less than 100 ppm of aromatic compounds for the counter current solvent extraction.

The static mixer used in the process of the present invention for co-current solvent extraction is usually selected from, but not limited to the group consisting of corrugated plate static mixer, multilayer static mixer, open design with helical static mixer and open design with blades static mixer.

Further an embodiment of the present invention provides a process for obtaining food grade hexane, comprising: treating a hydrocarbon feed having a boiling point in the range of 50° C. to 140° C. to obtain a mercaptan free hydrocarbon feed by converting mercaptan content of the hydrocarbon feed into disulfide; fractionating the mercaptan free hydrocarbon feed having a boiling point in the range of 50° C. to 140° C. to obtain a hydrocarbon fraction having boiling point in the range of 63° C. to 69° C. and having 3%-15% (wt/wt) of aromatic compounds content; extracting the hydrocarbon fraction by counter current solvent extraction using sulfolane as a solvent to obtain a first raffinate phase; extracting the first raffinate phase by co-current solvent extraction which is carried out by co-currently mixing the sulfolane and the first raffinate phase in a weight ratio in the range of 2 to 10 to obtain a second raffinate phase; washing the second raffinate phase with water to obtain a food grade hexane containing less than 100 ppm aromatic compounds; and recycling a part of the food grade hexane containing less than 100 ppm of aromatic compounds for the counter current solvent extraction.

Another embodiment of the present invention provides a process for obtaining food grade hexane, comprising: treating a hydrocarbon feed having a boiling point in the range of 50° C. to 140° C. to obtain a mercaptan free hydrocarbon feed by converting mercaptan content of the hydrocarbon feed into disulfide; fractionating the mercaptan free hydrocarbon feed having a boiling point in the range of 50° C. to 140° C. to obtain a hydrocarbon fraction having boiling point in the range of 63° C. to 69° C. and having 3%-15% (wt/wt) of aromatic compounds content; extracting the hydrocarbon fraction by counter current solvent extraction is carried out at a temperature in the range of 50° C. to 110° C. using sulfolane as a solvent to obtain a first raffinate phase; extracting the first raffinate phase by co-current solvent extraction using sulfolane as a solvent to obtain a second raffinate phase; washing the second raffinate phase with water to obtain a food grade hexane containing less than 100 ppm aromatic compounds; and recycling a part of the food grade hexane containing less than 100 ppm of aromatic compounds for the counter current solvent extraction.

Yet another embodiment of the present invention provides a process for obtaining food grade hexane, comprising: treating a hydrocarbon feed having a boiling point in the range of 50° C. to 140° C. to obtain a mercaptan free hydrocarbon feed by converting mercaptan content of the hydrocarbon feed into disulfide; fractionating the mercaptan free hydrocarbon feed having a boiling point in the range of 50° C. to 140° C. to obtain a hydrocarbon fraction having boiling point in the range of 63° C. to 69° C. and having 3%-15% (wt/wt) of aromatic compounds content; extracting the hydrocarbon fraction by counter current solvent extraction using sulfolane as a solvent to obtain a first raffinate phase; extracting the first raffinate phase by co-current solvent extraction is carried out at a temperature in the range of 50° C. to 110° C. using sulfolane as a solvent to obtain a second raffinate phase; washing the second raffinate phase with water to obtain a food grade hexane containing less than 100 ppm aromatic compounds; and recycling a part of the food grade hexane containing less than 100 ppm of aromatic compounds for the counter current solvent extraction.

The present invention further provides a process for obtaining food grade hexane, comprising: treating a hydrocarbon feed having a boiling point in the range of 50° C. to 140° C. to obtain a mercaptan free hydrocarbon feed by converting mercaptan content of the hydrocarbon feed into disulfide; fractionating the mercaptan free hydrocarbon feed having a boiling point in the range of 50° C. to 140° C. to obtain a hydrocarbon fraction having boiling point in the range of 63° C. to 69° C. and having 3% to 15% wt/wt of aromatic compounds content; extracting the hydrocarbon fraction by counter current solvent extraction using sulfolane as a solvent at a temperature in the range of 50° C. to 110° C. to obtain a first raffinate phase; extracting the first raffinate phase by co-current solvent extraction using sulfolane as a solvent at a temperature in the range of 50° C. to 110° C. to obtain second raffinate phase; and washing the second raffinate phase with water to obtain a food grade hexane containing less than 100 ppm of aromatic compounds.

The present invention further provides a process for obtaining food grade hexane, comprising: treating a hydrocarbon feed having a boiling point in the range of 50° C. to 140° C. to obtain a mercaptan free hydrocarbon feed by converting mercaptan content of the hydrocarbon feed into disulfide; fractionating the mercaptan free hydrocarbon feed having a boiling point in the range of 50° C. to 140° C. to obtain a hydrocarbon fraction having boiling point in the range of 63° C. to 69° C. and having 3% to 15% wt/wt of aromatic compounds content; extracting the hydrocarbon fraction by counter current solvent extraction using sulfolane as a solvent at a temperature in the range of 50° C. to 110° C. to obtain a first raffinate phase; extracting the first raffinate phase by co current solvent extraction using sulfolane as a solvent at a temperature in the range of 50° C. to 110° C. to obtain second raffinate phase; washing the second raffinate phase with water to obtain a food grade hexane containing less than 100 ppm of aromatic compounds; and recycling a part of the food grade hexane containing less than 100 ppm aromatic compounds for the counter current solvent extraction.

The present invention also provides a process for obtaining' food grade hexane, comprising: treating a hydrocarbon feed having a boiling point in the range of 50° C. to 140° C. to obtain a mercaptan free hydrocarbon feed by converting mercaptan content of the hydrocarbon feed into disulfide; fractionating a hydrocarbon feed having a boiling point in the range of 50° C. to 140° C. to obtain a hydrocarbon fraction having boiling point in the range of 63° C. to 69° C. and having 3%-15% (wt/wt) of aromatic compounds content; extracting the hydrocarbon fraction by counter current solvent extraction using sulfolane as a solvent to obtain a first raffinate phase; extracting the first raffinate phase by co-current solvent extraction using sulfolane as a solvent to obtain a second raffinate phase; and washing the second raffinate phase with water to obtain a food grade hexane containing less than 100 ppm of aromatic compounds.

The present invention further provides a process for obtaining a food grade hexane, comprising: treating a hydrocarbon feed having a boiling point in the range of 50° C. to 90° C. to obtain a mercaptan free hydrocarbon feed by converting mercaptan content of the hydrocarbon feed into disulfide; fractionating the mercaptan free hydrocarbon feed having a boiling point in the range of 50° C. to 90° C. to obtain a hydrocarbon fraction having boiling point in the range of 63° C. to 69° C. and having 3% to 15% wt/wt of aromatic compounds content; extracting the hydrocarbon fraction by counter current solvent extraction using sulfolane as a solvent at a temperature in the range of 50° C. to 110° C. to obtain a first raffinate phase; extracting the first raffinate phase by co current solvent extraction using sulfolane as a solvent at a temperature in the range of 50° C. to 110° C. to obtain second raffinate phase; and washing the second raffinate phase with water to obtain a food grade hexane containing less than 100 ppm of aromatic compounds.

The present invention also provides a process for obtaining a food grade hexane, comprising: treating a hydrocarbon feed having a boiling point in the range of 50° C. to 90° C. to obtain a mercaptan free hydrocarbon feed by converting mercaptan content of the hydrocarbon feed into disulfide; fractionating the mercaptan free hydrocarbon feed having a boiling point in the range of 50° C. to 90° C. to obtain a hydrocarbon fraction having boiling point in the range of 63° C. to 69° C. and having 3% to 15% wt/wt of aromatic compounds content; extracting the hydrocarbon fraction by counter current solvent extraction using sulfolane as a solvent at a temperature in the range of 50° C. to 110° C. to obtain a first raffinate phase; extracting the first raffinate phase by co current solvent extraction using sulfolane as a solvent at a temperature in the range of 50° C. to 110° C. to obtain second raffinate phase; washing the second raffinate phase with water to obtain a food grade hexane containing less than 100 ppm of aromatic compounds; and recycling a part of the food grade hexane containing less than 100 ppm aromatic compounds for the counter current solvent extraction.

The recycling of a food grade hexane having less than 100 ppm of aromatic compounds increases the effective solvent to feed ratio.

In the present invention the use of static mixer before raffinate wash column enhances the separation of aromatics.

The present invention provides a process for obtaining food grade hexane by extraction of aromatic compounds from naphtha range petroleum feed stock using solvent like NMP, sulfolane, and glycol.

The present invention provides a process for obtaining food grade hexane having less than 100 ppm of aromatic compounds where the solvent used for counter current solvent extraction and co-current solvent extraction is same.

The present invention provides a process for obtaining food grade hexane having less than 100 ppm of aromatic compounds where the counter current solvent extraction is carried out in multi stage sieve tray column and the co-current solvent extraction is carried out in static mixer, preferably corrugated plate type static mixer.

The static mixer used in the present invention contains minimum four numbers of mixing elements. A static mixer with efficient cross mixing is employed in a suitable position to increase the extraction of aromatics from first raffinate phase.

The static mixer used in the present invention is preferably, corrugated plate type static mixer having at least four mixing elements in number. The use of corrugated plate type static mixer enhances the separation of aromatics specifically benzene from first raffinate phase.

The process of the present invention is a cost effective process, since the refineries using sulfolane as solvent for producing food grade hexane can easily shift to the process of the present invention, without incurring any substantial cost. The process of the present invention is a cost effective process because it does not involve expensive apparatus as well as expensive reagents.

The term hydrocarbon fraction as used in the present invention contains a food grade hexane fraction and other contaminants. In general art, the 'hydrocarbon fraction having boiling point in the range of 63 to 69° C. and having 3-15% (wt/wt) of aromatic compounds content' and food grade hexane having boiling point in the range of 63 to 69° C. and having 3-15% (wt/wt) of aromatic compounds content are used interchangeable.

The schematic presentation of the process of the present invention is show in FIG. 1. In this scheme the hydrocarbon feed having boiling point in the range of 50 to 140° C. is first processed to remove mercaptans in column A and thereafter fractionated in columns B and C to get a hydrocarbon fraction having boiling point in the range of 63 to 69° C. and having 3-15% (wt/wt) of aromatic compounds content. The hydrocarbon fraction is routed to extractor where it is contacted counter currently with lean sulfolane solvent. The first extract phase, thus obtained is distilled in a distillation column under vacuum to recover the extract hydrocarbons while the solvent is recirculated back to the extractor. The first raffinate phase is contacted co-currently with sulfolane in a static mixer and separated in second raffinate phase and second extract phase. The second raffinate phase from the static mixer is water washed in a raffinate wash column to get finished product. In the most preferred embodiment the raffinate phase is partially recycled back to the extractor.

The solvent to feed ratio may range from 2 to 10 by weight and preferably between 2.5 and 5.5 by weight. The temperature in the contacting zone may range from 50° C. to 110° C., preferably in the range of 70° C. to 100° C.

The hydrocarbon feed is introduced through line 1 to the column A to convert mercaptans to disulfides. Thereafter the mercaptan free hydrocarbon feed is introduced to splitter B followed by splitter C through line 2 where it is fractionated in 63° C. to 69° C. cut. 63° C. to 69° C. cut which is known as hydrocarbon fraction is sent to extractor D through line 5 and lean solvent is introduced to column D via line 21 where the two streams meet counter currently. The extractor is a multistage sieve tray column. The first raffinate and first extract phase, thus produced, are separately withdrawn through lines 10 and 11 respectively. First raffinate phase which leaves the extractor D is sent to static mixer E via line 10. Lean solvent is introduced to static mixer E via line 9 where two streams meet co currently. The mixture is sent to a separating vessel F via line 12 where second raffinate phase and second extract phase are separately withdrawn through lines 13 and 14 respectively. Second raffinate phase from separating vessel F is sent to raffinate wash column G via line 13. Water is sent to column G via line 15 where it meets raffinate phase counter currently. The wash water containing sulfolane is recycled to solvent recovery column H via line 17. The water washed raffinate is partially recycled back to the extractor through line 8 and remaining is forwarded through line 16 as a food grade hexane containing less than 100 ppm of aromatic compounds.

The extract phase obtained from the extractor D and separating vessel F is introduced via lines 11 and 14 respectively in the solvent recovery column H where solvent free extract is forwarded to a separation vessel I via line 18. From the vessel I water layer is removed via line 15 and the hydrocarbon feed is partly recycled to the solvent recovery column H via line 19 and partly removed via line 20. The regenerated selective solvent obtained as bottom product from column H is sent to extractor D and static mixer E via lines 21 and 9 respectively.

Under the conditions employed in the process of the invention the aromatic compounds left in the second raffinate from static mixer is less than 100 ppm. Thus, the food grade hexane (63-69° C.) obtained by the process of the present invention contains less than 100 ppm benzene.

Figure 2:
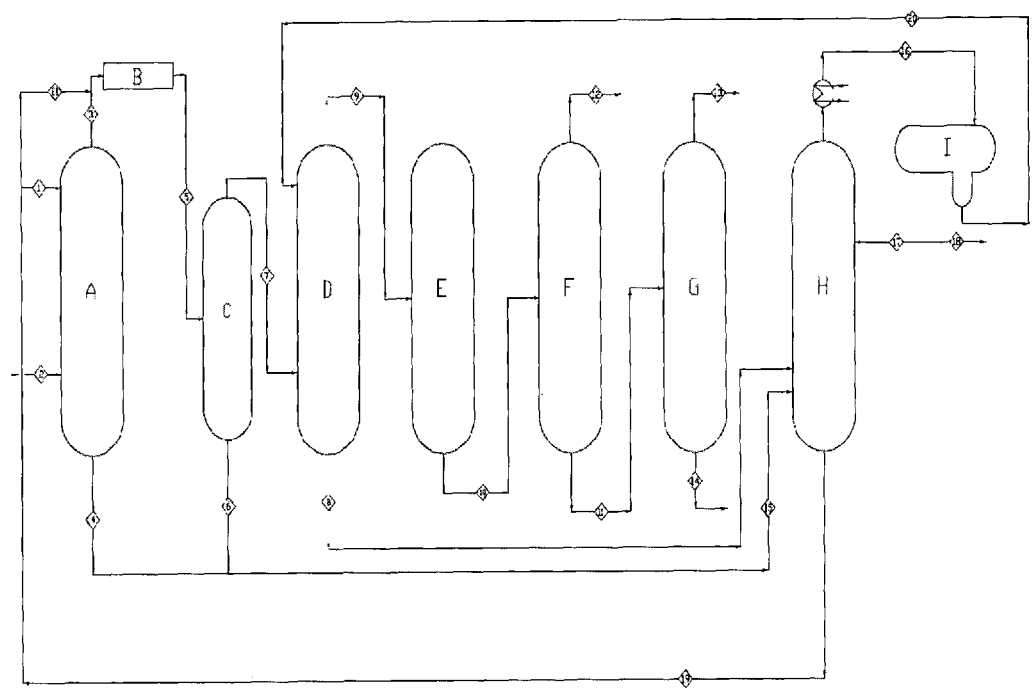
FIG. 2 is a schematic illustration of the process for obtaining food grade hexane containing 150-400 ppm aromatic compounds.
Figure 3:
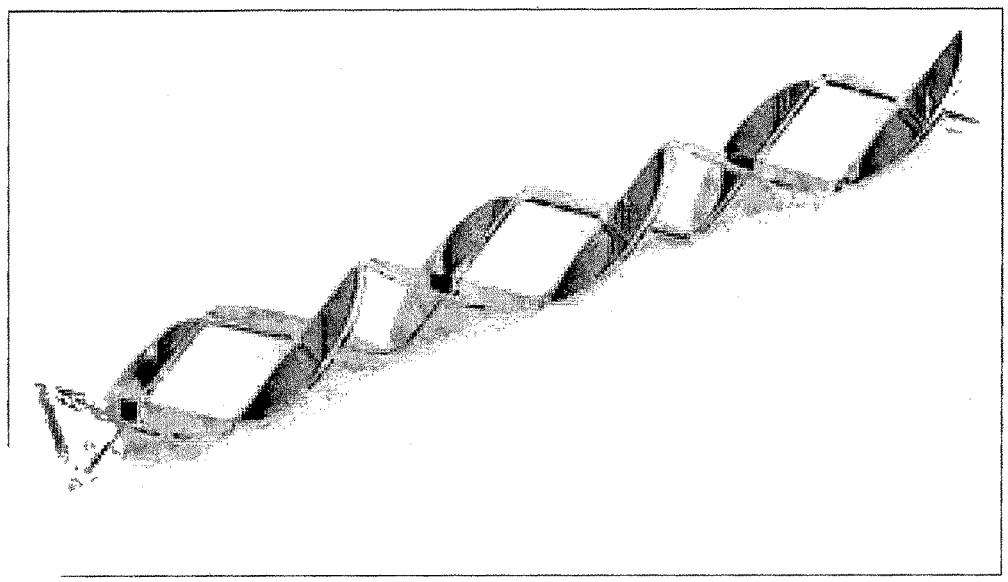
FIG. 3 shows a static mixer which can be used for efficient cross mixing in the process of the present invention.

FIG. 2 shows a process of obtaining food grade hexane in which the two stage solvent extraction is carried out before the fractionation of the hydrocarbon feed. The process shown in FIG. 2 is similar to the process of the present invention except the position of solvent extraction. In the process shown in FIG. 2, is as follows:

Hydrocarbon feed boiling in the range of 50 to 140° C. is introduced through line 2 into extractor A and lean solvent is introduced to extractor A via line 1 where the two streams meet counter currently. The extractor is a multistage sieve tray column. The first raffinate and first extract phase, thus produced, are separately withdrawn through lines 3 and 4 respectively. First raffinate phase which leaves the extractor A is sent to static mixer B via line 3. Lean solvent is introduced to static mixer B via line 21 where two streams meet co currently. The mixture is sent to a separating vessel C via line 5 where second extract and second raffinate phases are separately withdrawn through lines 6 and 7 respectively. Second raffinate phase from separating vessel C is water washed in raffinate wash column D. The water washed second raffinate is sent to column E via line 9 where mercaptans are converted to disulfides and then enters the column F via line 10 where it gets fractionated to 63$^{-\circ}$ C. and 63$^{+\circ}$ C. 63$^{-\circ}$ C. is forwarded through line 12 and 63$^{+\circ}$ C. fraction is sent to column G via line 11 where it gets fractionated to 63 to 69° C. cut which is forwarded through line 13 as food grade hexane and 69$^{+\circ}$ C. which is forwarded through line 14. Water is sent to column D via line 20 where it meets raffinate phase counter currently. The wash water containing sulfolane is recycled to solvent recovery column H via line 8.

The extract phase obtained from the extractor A and separating vessel C is forwarded through lines 4 and 6 respectively and jointly introduced via lines 15 in the solvent recovery column H where solvent free extract is forwarded to a separation vessel I via line 16. From the vessel water layer is removed via line 20 and the hydrocarbon layer is partly recycled to the solvent recovery column H via line 17 and partly removed via line 18. The regenerated selective solvent obtained as bottom product from column H forwarded via line 19 and sent to extractor A and static mixer B via lines 1 and 21 respectively.

Under the conditions employed in the process of the invention the aromatic compounds left in the second raffinate from static mixer is less than 100 ppm. Due to azeotrope formation aromatic compound content gets enriched in food grade hexane (63-69° C.) fraction obtained from fractionator G. Thus aromatic content in food grade hexane obtained by this process is in the range of 150 to 400 ppm, which is not desired.

The comparative study of the two processes disclosed in FIG. 1 and FIG. 2 shows that the mere two stage solvent extraction will not give the food grade hexane having aromatic content less than 100 ppm. The particular position of two stage solvent extraction, i.e. after the fractionation of the hydrocarbon feed, is important to obtain the desired product.

EXAMPLES

The following examples are given by way of illustration of the present invention and should not be construed to limit the scope of present disclosure. It is to be understood that both the foregoing general description and the following detailed description are exemplary and explanatory only and are intended to provide further explanation of the claimed subject matter.

Example 1

The process used in this example is as per the schematic representation of FIG. 1. The hydrocarbon feed (50-90° C.) containing about 15 wt. % of total aromatics is fed to column A via line 1 at a rate of 300 tons per day where mercaptans are converted to disulfides using Kero Merox process, as disclosed in U.S. Pat. No. 4,088,569. Thereafter the mercaptan free hydrocarbon feed is fed to fractionator B via line 2 where it splits into two fractions of 63$^{-\circ}$ C. and 63$^{+\circ}$ C. boiling range. The overhead product is forwarded via line 3 and the bottom stream is fed to splitter C via line 4 where it is fractionated into two fractions of 63-69° C. boiling range and above 69° C. The bottom product is forwarded via line 6 and the overhead product (hydrocarbon fraction) containing about 7 wt. % aromatics is fed into the bottom of sieve tray solvent extractor D at a rate of 150 tons per day where it is contacted counter currently with the solvent stream of sulfolane flowing in from the top of the extraction column at a rate of 1140 tons per day at 90° C. through line 21. The resulting, first raffinate phase is withdrawn from the top of the column at a rate of 120 tons per day via line 10. The first raffinate phase is sent to static mixer E via line 10 where it is contacted co currently with sulfolane at a flow rate of 480 tons per day coming through line 9. The mixture is sent to settler F via line 12 where it gets separated in second raffinate phase and second extract phase. The second raffinate phase from the static mixer containing less than 100 ppm benzene is sent to raffinate wash column (RWC) G via line 13, where it comes in contact with water flowing in from the top via line 15. The RWC operates at 45° C. The water washed raffinate phase is withdrawn from the top of column G via line 16 and recycled to the extractor D via line 8 to meet the minimum throughput of 300 tons per day to the extraction column D. Once the column is stabilized 50 wt. % of the raffinate phase from RWC containing aromatics in traces is recycled and rest is forwarded as food grade hexane with less than 100 ppm aromatics via line 16. The feed entering to the extraction column contains about 3.5 wt. % aromatics. Thus the food grade hexane produced by this process invention contains less than 100 ppm aromatics especially benzene. The wash water containing solvent from the bottom of the column G is sent to solvent recovery column H via line 17. The extract phase from the bottom of the extractor D and from the bottom of the settler F is sent to solvent recovery column H via lines 11 and 14 respectively for solvent recovery.

The process produces food grade hexane (FGH) containing less than 100 ppm aromatic compounds.

Example 2

The process employed in this example is as per FIG. 2. The hydrocarbon feed (50-90° C.) containing about 15 wt. % of total aromatics is fed to a sieve tray extractor A via line 2 at a rate of 300 tons per day where it is contacted counter currently with the solvent stream of sulfolane flowing in from the top of the extractor at a rate of 1350 tons per day at 93° C. temperature via line 1. The resulting first raffinate phase is withdrawn from the top of the column at a rate of 171 tons per day via line 3 and the first extract phase is withdrawn from the bottom at a rate of 1479 tons per day via line 4. The first raffinate phase is sent to static mixer B via line 3 where it is contacted co currently with sulfolane at a flow rate of 650 tons per day coming through line 21. The mixture is sent to settler C via line 5 where it gets separated in second raffinate phase and second extract phases. The second raffinate phase from the static mixer containing less than 100 ppm benzene is sent to raffinate wash column (RWC) D via line 7 at a rate of 136 tons per day, where it comes in contact with water flowing in from the top via line 20. The RWC operates at 45° C. The water washed raffinate phase is withdrawn from the top of column D via line 9 at a rate of 130 tons per day. The washed raffinate is sent to column E to convert mercaptans into disulfides via line 9 and thereafter sent to fractionator F via line 10 where it is fractionated in $63^{-\circ}$ C. and $63^{+\circ}$ C. cuts. $63^{-\circ}$ C. cut is forwarded through line 12 and $63^{+\circ}$ C. cut is sent to splitter G through line 11 where it is again fractionated to 63-69° C. and $69^{+\circ}$ C. fractions. 63-69° C. fraction is forwarded through line 13 as food grade hexane containing 200 ppm benzene at a rate of 80 tons per day. The wash water containing solvent from the bottom of the column D is sent to solvent recovery column H via line 8. The extract phase from the bottom of the extractor A and from the bottom of the settler C is sent to solvent recovery column H jointly through line 15 for solvent recovery.

The food grade hexane (FGH) produced in this process scheme contains aromatics specially benzene around 200 ppm.

Example 3

The process used in this example is as per the schematic representation of FIG. 2. The hydrocarbon feed (50-90° C.) containing about 15 wt. % of total aromatics is fed to a sieve tray extractor A via line 2 at a rate of 282 tons per day where it is contacted counter currently with the solvent stream of sulfolane flowing in from the top of the extractor at a rate of 913 tons per day at 93° C. temperature via line 1. The resulting first raffinate phase is withdrawn from the top of the column at a rate of 201 tons per day via line 3 and the first extract phase is withdrawn from the bottom at a rate of 994 tons per day via line 4. The first raffinate phase is sent to raffinate wash column D bypassing static mixer B. The water washed raffinate phase is withdrawn from the top of column D via line 9 at a rate of 190 tons per day. The washed raffinate is sent to column E to convert mercaptans into disulfides via line 9 and thereafter sent to fractionator F via line 10 where it is fractionated in $63^{-\circ}$ C. and $63^{+\circ}$ C. cuts. $63^{-\circ}$ C. cut is forwarded through line 12 and $63^{+\circ}$ C. cut is sent to splitter G through line 11 where it is again fractionated to 63-69° C. and $69^{+\circ}$ C. fractions. 63-69° C. fractions are forwarded through line 13 as food grade hexane containing 350 ppm benzene at a rate of 131 tons per day.

Example 4

The process used in this example is as per the schematic representation of FIG. 1. The hydrocarbon feed (50-90° C.) containing about 15 wt. % of total aromatics is fed to column A via line 1 at a rate of 250 tons per day where mercaptans are converted to disulfides using Kero Merox process. Thereafter mercaptan free hydrocarbon feed is fed to fractionator B via line 2 where it splits into two fractions of $63^{-\circ}$ C. and $63^{+\circ}$ C. boiling range. The overhead product is forwarded via line 3 and the bottom stream is fed to splitter C via line 4 where it is fractionated into two fractions of 63-69° C. boiling range and above 69° C. The bottom product is forwarded via line 6 and the overhead product (hydrocarbon fraction) containing about 11 wt. % aromatics is fed into the bottom of sieve tray solvent extractor D at a rate of 150 tons per day where it is mixed with 167 tons of recycle phase containing traces of benzene from raffinate wash column (RWC) through line 8 and contacted counter currently with the solvent stream of sulfolane flowing in from the top of the extraction column at a rate of 1231 tons per day at 90° C. through line 21. The resulting raffinate phase is withdrawn from the top of the column at a rate of 272 tons per day via line 10 and sent to raffinate wash column G bypassing static mixer E to remove dissolved sulfolane. Water washed raffinate is collected through line 16 which is partly recycled to column D through line 8 and rest is collected as food grade hexane containing 170 ppm benzene.

This example shows that if the co-current solvent extraction is not carried out in the process at the desired stage the food grade hexane obtained will contain aromatic content more than 100 ppm which is not desired.

This shows that the process of Example 1 is the desired process as compared to the process of example 2, 3 and 4.

Although the subject matter has been described in considerable detail with reference to certain preferred embodiments thereof, other embodiments are possible. As such, the spirit and scope of the appended claims should not be limited to the description of the preferred embodiment contained therein.

We claim:

1. A process for obtaining food grade hexane, comprising:
   fractionating a hydrocarbon feed having a boiling point in the range of 50° C. to 140° C. to obtain a hydrocarbon fraction having boiling point in the range of 63° C. to 69° C. and having 3%-15% (wt/wt) of aromatic compounds content;
   extracting the hydrocarbon fraction by counter current solvent extraction using sulfolane as a solvent to obtain a first raffinate phase;
   extracting the first raffinate phase by co-current solvent extraction using sulfolane as a solvent to obtain a second raffinate phase; and
   washing the second raffinate phase with water to obtain a food grade hexane containing less than 100 ppm weight of aromatic compounds.

2. The process as claimed in claim 1, further comprising; recycling a part of the food grade hexane containing less than 100 ppm weight of aromatic compounds for the counter current solvent extraction.

3. The process as claimed in claim 1, wherein the hydrocarbon feed is treated to obtain a mercaptan free hydrocarbon feed by converting mercaptan content of the hydrocarbon feed into disulfide.

4. The process as claimed in claim 1, wherein the hydrocarbon feed has a boiling point in the range of 50° C. to 90° C.

5. The process as claimed in claim 1, wherein the hydrocarbon feed is a naphtha range petroleum stock.

6. The process as claimed in claim 1, wherein the aromatic compounds is selected from the group consisting of benzene and toluene or mixtures thereof.

7. The process as claimed in claim 1, wherein the counter current solvent extraction is by using an extractor.

8. The process as claimed in claim 7, wherein the extractor is selected from the group consisting of rotating disc column, packed column, Sieve tray column, pulsed column, and Karr reciprocating column.

9. The process as claimed in claim 1, wherein the counter current solvent extraction is carried out by counter currently mixing the sulfolane and the hydrocarbon fraction in a weight ratio in the range of 2 to 10.

10. The process as claimed in claim 1, wherein the co-current solvent extraction is by using a static mixer.

11. The process as claimed in claim 10, wherein the static mixer is selected from the group consisting of corrugated plate static mixer, multilayer static mixer, open design with helical static mixer and open design with blades static mixer.

12. The process as claimed in claim 1, wherein the co-current solvent extraction is carried out by co-currently mixing the sulfolane and the first raffinate phase in a weight ratio in the range of 2 to 10.

13. The process as claimed in claim 1, wherein the counter current solvent extraction and the co-current solvent extraction is carried out at a temperature in the range of 50° C. to 110° C.

14. A process for obtaining food grade hexane, comprising:
   treating a hydrocarbon feed having a boiling point in the range of 50° C. to 90° C. to obtain a mercaptan free hydrocarbon feed by converting mercaptans content of the hydrocarbon feed into disulfides;
   fractionating the mercaptan free hydrocarbon feed to obtain a hydrocarbon fraction having boiling point in the range of 63° C. to 69° C. and having 3% to 15% wt/wt of aromatic compounds content;
   extracting the hydrocarbon fraction by counter current solvent extraction using sulfolane as a solvent at a temperature in the range of 50° C. to 110° C. to obtain a first raffinate phase;
   extracting the first raffinate phase by co current solvent extraction using sulfolane as a solvent at a temperature in the range of 50° C. to 110° C. to obtain a second raffinate phase; and
   washing the second raffinate phase with water to obtain a food grade hexane containing less than 100 ppm weight of aromatic compounds.

15. The process as claimed in claim 14 further comprising:
   recycling a part of the food grade hexane containing less than 100 ppm weight of aromatic compounds for the counter current solvent extraction.

* * * * *